United States Patent [19]

Hussain

[11] 4,428,883

[45] Jan. 31, 1984

[54] NOVEL METHOD OF ADMINISTERING β-BLOCKERS AND NOVEL DOSAGE FORMS CONTAINING SAME

[75] Inventor: Anwar A. Hussain, Lexington, Ky.

[73] Assignee: The University of Kentucky Research Foundation, Lexington, Ky.

[21] Appl. No.: 241,413

[22] Filed: Mar. 6, 1981

[51] Int. Cl.³ .................. A61K 27/00; A61K 31/15; A61K 31/40; A61K 31/47; A61K 31/135; A61K 31/165; A61K 31/435; A61K 31/475; A61K 47/00; C07C 143/90; C11D 1/28; C09F 5/00

[52] U.S. Cl. .................. 424/248.51; 260/404.5; 260/401; 424/256; 424/258; 424/262; 424/274; 424/324; 424/327; 424/330; 424/358; 424/362

[58] Field of Search ............. 424/14, 28, 34, 39, 424/230, 248.51, 274, 324, 358, 362; 260/501.7, 404.5 A, 401 S, 324, 248.51, 262, 256, 258, 327, 330, 274, 358, 362

[56] References Cited

U.S. PATENT DOCUMENTS 3,676,493  7/1972  Smith ................. 260/404.5 R
4,012,444  3/1977  Lunts ................. 424/324
4,127,674  11/1978 Leopold ............... 424/324
4,161,530  7/1979  Koella ................ 424/274
4,250,163  2/1981  Nagai ................. 424/14

FOREIGN PATENT DOCUMENTS 979389  1/1965  United Kingdom .

OTHER PUBLICATIONS

Stern, Arzmit. Forsch, vol. 24, 1974, pp. 70–71.
Black, Brit. J. Pharmacol., (1965) 25, pp. 577–591.

*Primary Examiner*—Stanley J. Friedman
*Attorney, Agent, or Firm*—Burns, Doane, Swecker & Mathis

[57] ABSTRACT

The invention provides a novel method of administering selected known adrenergic β-receptor blocking agents, such as dichloroisoproterenol, pronethalol, sotalol and alprenolol, which are of use in the treatment of angina pectoris, arrhythmias, hypertension and other cardiac conditions, and migraine. The invention further provides novel dosage forms of those β-blockers which are adapted for nasal administration and which include solutions, suspensions, gels and ointments.

61 Claims, No Drawings

NOVEL METHOD OF ADMINISTERING β-BLOCKERS AND NOVEL DOSAGE FORMS CONTAINING SAME

BACKGROUND OF THE INVENTION

1. Field of the Invention

The present invention relates to a novel method of administering selected known adrenergic β-receptor blocking agents, and to novel dosage forms containing such agents adapted for nasal administration.

2. Background Art

A number of β-adrenergic blocking agents are known. Such agents are widely used therapeutically, chiefly in the management of hypertension and in the treatment of angina pectoris, arrhythmias and other cardiac conditions, and also possibly in the treatment of migraine. Unfortunately, however, these known β-blockers are inefficiently and variably absorbed from oral dosage forms, probably because of extensive metabolism of the drug in the gastrointestinal tract and/or extensive effects of the first pass through the liver.

The present inventor and his co-workers have previously reported that one widely used β-blocker, propranolol, can be effectively administered in nasal dosage form. Nasal administration of propanolol has been found to provide enhanced bioavailability and minimized variations in blood levels as compared to oral administration. See copending Hussain et al. Application Ser. No. 063,176, filed Aug. 3, 1979; Hussain et al. *J. Pharm. Sci.*, Vol. 68, No. 8, September, 1979, page 1196; Hussain et al, *J. Pharm. Sci.*, Vol. 69, No. 10, October, 1980, page 1240; Hussain et al, *J. Pharm. Sci.*, Vol. 69, No. 12, December, 1980, pages 1411–1413.

SUMMARY OF THE INVENTION

Surprisingly, the present inventor has now found that yet other adrenergic β-receptor blocking agents can be effectively administered nasally. More specifically, the present inventor has found that selected β-blockers, which differ substantially in chemical structure from propanolol and which also have significantly different biological profiles [e.g., they may differ in potency, β-blocker receptor selectivity ($β_1$ versus $β_2$), agonist properties and/or membrane-stabilization activity] from that of propanolol, can nevertheless be advantageously formulated into novel nasal dosage forms and administered nasally to provide enhanced bioavailability and minimized variations in blood levels as compared to oral dosage forms of those β-blockers, while at the same time providing relative ease of administration when compared to the intravenous route. The novel nasal dosage forms of the invention can be solutions, suspensions, ointments or gels adapted for nasal administration.

DETAILED DESCRIPTION OF THE INVENTION

The selected β-blockers for use in the compositions and methods of the present invention are dichloroisoproterenol (DCI), pronethalol, sotalol, oxprenolol, pindolol, metoprolol, nadoxolol, practolol, butoxamine, alprenolol, metalol, nifenalol, acebutolol, atenolol, bunolol, carteolol, labetalol, pamatolol, timolol, tiprenolol, xipranolol and bupranolol. Any pharmaceutically acceptable form of these β-blockers can be employed, i.e. the free base or a pharmaceutically acceptable salt or ester thereof (e.g., oxprenolol hydrochloride, alprenolol hydrochloride, metoprolol tartrate, nadoxolol hydrochloride, pamatolol sulfate, timolol maleate, bupranolol hydrochloride, etc.); generally, the selected β-blocker is employed in the instant compositions and method in the pharmaceutically acceptable form which has previously been found most advantageous for oral or intravenous use. The structural formulae for the free bases encompassed by the present invention are set forth below:

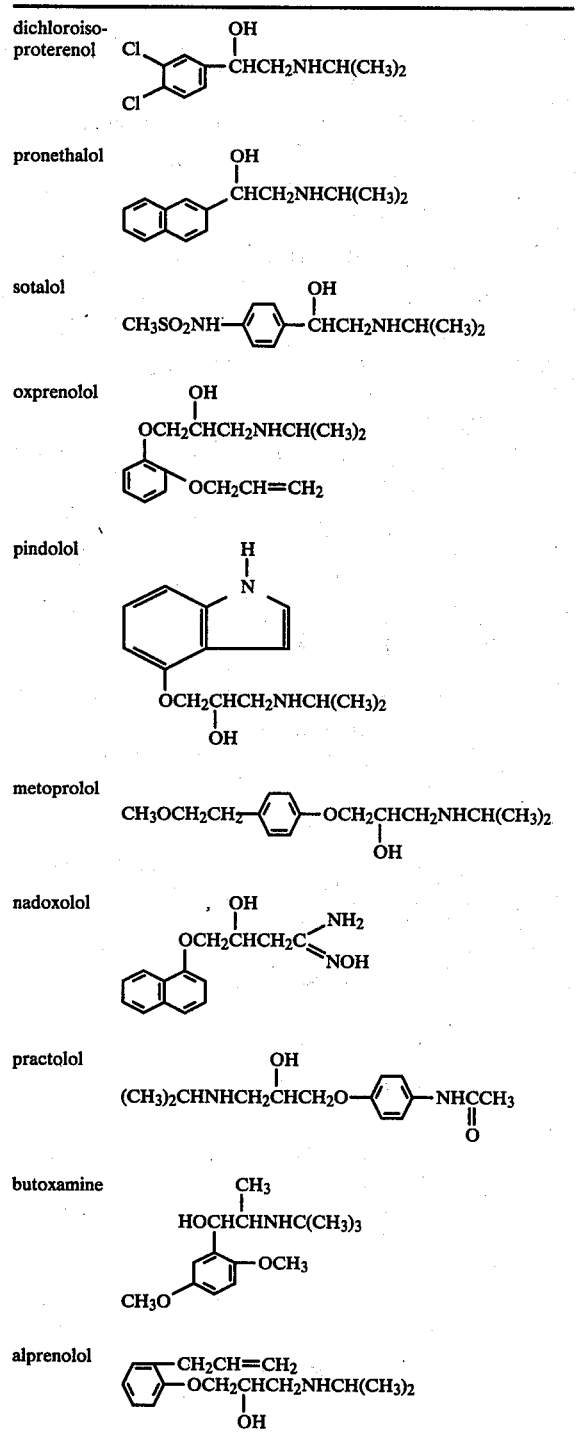

-continued metalol 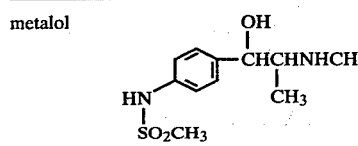

nifenalol 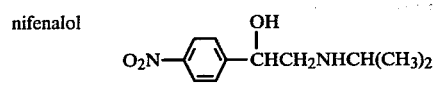

acebutolol 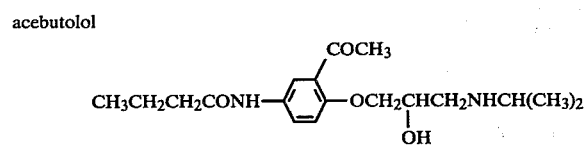

atenolol 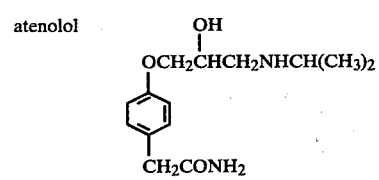

bunolol 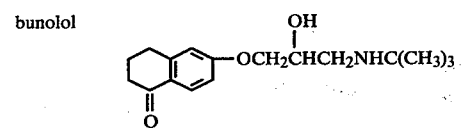

carteolol 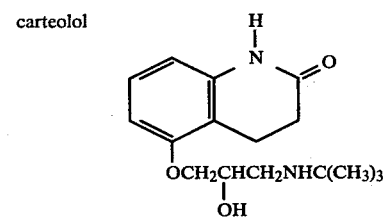

labetalol 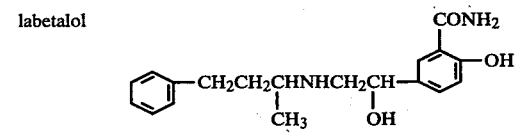

pamatolol 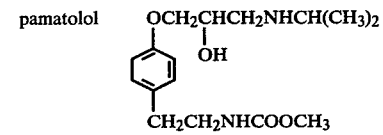

timolol 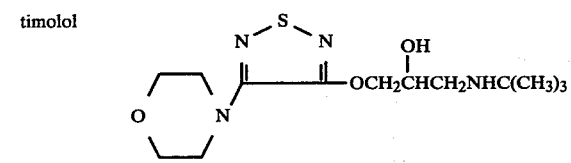

tiprenolol 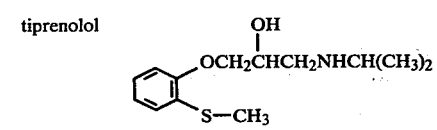

-continued xipranolol 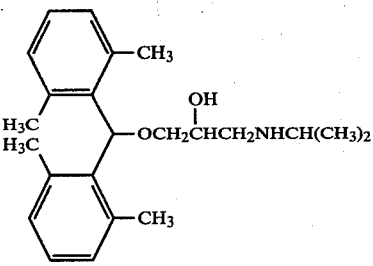

bupranolol 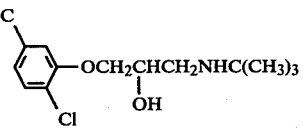

These β-blockers can be made by well-known methods.

In accord with the present invention, the selected β-blockers named supra can be administered nasally with results considerably superior to those obtained with oral administration in terms of enhanced drug bioavailability and minimization of blood level variations, thus enabling use of these β-blockers at lower dosage levels than was previously possible except in the case of intravenous administration. It would appear that these selected β-blockers are rapidly absorbed from the nasal mucosa into systemic blood without first-pass metabolism.

Any of the selected β-blockers identified above can be conveniently administered nasally to warm-blooded animals by formulating it into a nasal dosage form comprising the desired β-blocker, in an effective β-blocking amount, together with a nontoxic pharmaceutically acceptable nasal carrier therefor. As indicated earlier, the β-blocker can be employed in the form of the free base or in the form of a pharmaceutically acceptable salt or ester thereof. Suitable nontoxic pharmaceutically acceptable nasal carriers will be apparent to those skilled in the art of nasal pharmaceutical formulations. For those not skilled in the art, reference is made to the text entitled "REMINGTON'S PHARMACEUTICAL SCIENCES", 14th edition, 1970. Obviously, the choice of suitable carriers will depend on the exact nature of the particular nasal dosage form desired, e.g., whether the β-blocker is to be formulated into a nasal solution (for use as drops or as a spray), a nasal suspension, a nasal ointment or a nasal gel. Preferred nasal dosage forms are solutions, suspensions and gels, which contain a major amount of water (preferably purified water) in addition to the active ingredient. Minor amounts of other ingredients such as pH adjusters (e.g., a base such as NaOH), emulsifiers or dispersing agents, buffering agents, preservatives, wetting agents and jelling agents (e.g., methylcellulose) may also be present. Most preferably, the nasal composition is isotonic, i.e. it has the same osmotic pressure as blood serum. If desired, sustained release nasal compositions, e.g. sustained release gels, can be readily prepared, preferably by employing the desired β-blocker in one of its relatively insoluble forms, such as the free base or an insoluble salt. When the free base is not sufficiently insoluble for sustained release compositions, or when a more highly insoluble form is desired, a long chain carboxylic acid salt of the desired β-blocker can be conveniently employed. The carboxylic acid portion of the salt preferably contains 10 to 20 carbon atoms. Such salts (e.g. stearates, palmitates etc.) can be readily synthesized, for example, by dissolving the hydrochloride salt of the β-blocker in water, then adding the alkali metal salt of the desired long chain carboxylic acid (e.g. sodium stearate). The corresponding long chain carboxylic acid salt which precipitates out of solution is removed by filtration. Alternatively, equimolar amounts of the β-blocker free base and the long chain carboxylic acid are combined in methanol. That mixture is then added to a small volume of water, causing the desired salt (e.g. β-blocker stearate) to precipitate out.

Examples of the preparation of typical nasal compositions containing selected β-blockers are set forth below. However, it is to be understood that these examples are given by way of illustration only and are not to be construed as limiting the invention either in spirit or in scope as many modifications both in materials and in methods will be apparent to those skilled in the art.

EXAMPLE 1

2 Grams of sotalol hydrochloride are dissolved in 80 ml of distilled water and the pH of the resultant solution is adjusted to 7.4 with dilute sodium hydroxide solution. A quantity of water sufficient to bring the total volume to 100 ml is then added and sufficient sodium chloride or other appropriate salt is added to adjust the solution to isotonicity. The solution is then sterilized by being passed through a 0.2 micron Millipore filter. The final composition contains 2 mg of sotalol hydrochloride per 0.1 ml of solution.

The above procedure is repeated using 2 grams of oxprenolol hydrochloride in place of the sotalol hydrochloride. The resultant composition contains 2 mg of oxprenolol hydrochloride per 0.1 ml of solution.

Repetition of the procedure of the first paragraph of this example using 4 grams of metoprolol tartrate in place of the sotalol hydrochloride affords a nasal composition containing 4 mg of metoprolol tartrate per 0.1 ml of solution.

EXAMPLE 2

15 Grams of alprenolol hydrochloride are combined with 80 ml of distilled water and the pH is adjusted to 4.5 with dilute sodium hydroxide solution. A quantity of water sufficient to bring the total volume to 100 ml is then added and sufficient sodium chloride is added to adjust the solution to isotonicity. The solution is then sterilized by being passed through a 0.2 micron Millipore filter. The resultant composition contains 15 mg of alprenolol hydrochloride per 0.1 ml.

The procedure described above is substantially repeated, except that 30 grams of pronethalol hydrobromide are used in place of the alprenolol hydrochloride, affording a nasal composition containing 30 mg of pronethalol hydrobromide per 0.1 ml.

EXAMPLE 3

4 Grams of dichloroisoproterenol are dissolved in 80 ml of isotonic saline solution and the pH of the resultant solution is adjusted to 7.0–7.2 with dilute hydrochloric acid. A quantity of isotonic saline sufficient to bring the total volume to 100 ml is then added, and the solution is sterilized by being passed through a 0.2 micron Millipore filter. The resultant composition contains 4 mg of dichloroisoproterenol per 0.1 ml.

Repetition of the foregoing procedure utilizing 8 grams of sotalol in place of the dichloroisoproterenol affords a nasal composition containing 8 mg of sotalol per 0.1 ml.

The procedure of the first paragraph of this example is substantially repeated, save that 5 grams of pindolol are employed in place of the dichloroisoproterenol, to afford a nasal composition containing 5 mg of pindolol per 0.1 ml.

EXAMPLE 4

80 Grams of water are heated to 80° C. and 3.0 grams of Methocel are added, with stirring. The resultant mixture is allowed to stand at room temperature for 3 hours. Then, 1.84 grams of oxprenolol stearate are suspended in 20 grams of water, that suspension is added to the gel and thoroughly mixed, and the resultant viscous solution or gel is adjusted to isotonicity with sodium chloride. The sustained release composition thus obtained contains 1.84 mg of oxprenolol stearate per 0.1 ml.

The above procedure is substantially repeated, except that 2.0 rather than 3.0 grams of Methocel are employed, and 3.0 grams of sotalol palmitate are substituted for the oxprenolol stearate. The sustained release composition prepared in this manner contains 3.0 mg of sotalol palmitate per 0.1 ml.

Repetition of the procedure of the first paragraph of this example, but using 2 grams of nadoxolol stearate in place of the oxprenolol stearate, affords a sustained release composition containing 2 mg of nadoxolol stearate per 0.1 ml.

The procedure of the first paragraph of this example is substantially repeated, except that 1.84 grams of dichloroisoproterenol palmitate are employed in place of the oxprenolol stearate. The resultant sustained release composition contains 1.84 mg of dichloroisoproterenol palmitate per 0.1 ml.

Substitution of 20 grams of pronethalol myristate for the oxprenolol stearate used in the first paragraph of this example and substantial repetition of the procedure there detailed afford a sustained release composition containing 20 mg of pronethalol myristate per 0.1 ml.

EXAMPLE 5

The following are illustrative aqueous solutions of selected β-blockers suitable for use as nasal drops or nasal spray. In each case, the pH of the final composition is adjusted to 7.4. If desired, the solutions are adjusted to isotonicity.

| Ingredient | Amount |
|---|---|
| COMPOSITION A | |
| nadoxol hydrochloride | 500 mg |
| Tween 80 | 2 mg |
| methylcellulose | 20 mg |
| water, purified | 10 ml |
| COMPOSITION B | |
| bupranolol hydrochloride | 750 mg |
| Tween 80 | 3 mg |
| methylcellulose | 30 mg |
| water, purified | 10 ml |
| COMPOSITION C | |
| timolol maleate | 800 mg |
| Tween 80 | 3 mg |
| methylcellulose | 20 mg |
| water, purified | 10 ml |

Naturally, the therapeutic dosage range for nasal administration of the β-blockers according to the present invention will vary with the size of the patient, the condition for which the drug is administered and the particular β-blocker employed. Generally, the daily dosage will approximate the amounts previously employed for intravenous administration of the particular β-blocker involved. Thus, a typical dose of sotalol would be 1 to 10 mg administered nasally three times daily. The quantity of nasal dosage form needed to deliver the desired dose will of course depend on the concentration of β-blocker in the composition. The volume of solution or gel which would be needed to deliver the typical dose of sotalol specified above would be 0.05 to 0.5 ml of 2% solution or gel.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method for eliciting a systemic therapeutic β-adrenergic blocking response in a warm-blooded animal, which comprises nasally administering to said animal a systemically therapeutically effective β-adrenergic blocking amount of dichloroisoproterenol, pronethalol, sotalol, oxprenolol, pindolol, metoprolol, nadoxolol, practolol, butoxamine, alprenolol, metalol, nifenalol, acebutolol, atenolol, bunolol, carteolol, labetalol, pamatolol, timolol, tiprenolol, xipranolol or bupranolol, or a nontoxic pharmaceutically acceptable salt thereof.

2. A method as defined by claim 1 for eliciting a systemic therapeutic β-adrenergic blocking response in a warm-blooded animal, which comprises nasally administering to said animal a systemically therapeutically effective β-adrenergic blocking amount of dichloroisoproterenol, pronethalol, sotalol, oxprenolol, pindolol, alprenolol, metoprolol, nadoxolol, timolol or bupranolol, or a nontoxic pharmaceutically acceptable acid addition salt thereof.

3. A method as defined by claim 1 for eliciting a systemic therapeutic β-adrenergic blocking response in a warm-blooded animal, which comprises nasally administering to said animal a systemically therapeutically effective β-adrenergic blocking amount of a long-chain carboxylic acid salt of dichloroisoproterenol, pronethalol, sotalol, oxprenolol, pindolol, metoprolol, nadoxolol, practolol, butoxamine, alprenolol, metalol, nifenalol, acebutolol, atenolol, bunolol, carteolol, labetalol, pamatolol, timolol, tiprenolol, xipranolol or bupranolol, the carboxylic acid portion of said salt containing 10 to 20 carbon atoms.

4. A method for eliciting a systemic therapeutic β-adrenergic response in a warm-blooded animal which comprises nasally administering to said animal, a systemically therapeutically effective β-adrenergic blocking amount of a composition as defined.

5. A method as defined by claim 1, wherein said warm-blooded animal is afflicted with angina pectoris.

6. A method as defined by claim 1, wherein said warm-blooded animal is afflicted with arrhythmias.

7. A method as defined by claim 1, wherein said warm-blooded animal is afflicted with hypertension.

8. A method as defined by claim 1, wherein said warm-blooded animal is afflicted with migraine.

9. A pharmaceutically acceptable, sustained release nasal composition, in dosage unit form, for nasal administration to obtain a systemic therapeutic β-adrenergic blocking response in a warm-blooded animal, consisting essentially of, per nasal dosage unit, (i) a systemically therapeutically effective unit β-adrenergic blocking amount of a long chain carboxylic acid salt of dichloroisoproterenol, pronethalol, sotalol, oxprenolol, pindolol, metoprolol, nadoxol, practolol, butoxamine, alprenolol, metalol, nifenalol, acebutolol, atenolol, bunolol, carteolol, labetalol, pamatolol, timolol, tiprenolol, xipranolol or bupranolol, the carboxylic acid portion of said salt containing 10 to 20 carbon atoms, and (ii) a nontoxic pharmaceutically acceptable nasal carrier therefor, said composition being in the form of a nasal ointment or a nasal gel.

10. The composition as defined by claim 9, wherein said salt is a stearate.

11. The composition as defined by claim 9, wherein (i) is a systemically therapeutically effective unit β-adrenergic blocking amount of a long chain carboxylic acid salt of dichloroisoproterenol.

12. The composition as defined by claim 9, wherein (i) is a systemically therapeutically effective unit β-adrenergic blocking amount of a long chain carboxylic acid salt of pronethalol.

13. The composition as defined by claim 9, wherein (i) is a systemically therapeutically effective unit β-adrenergic blocking amount of a long chain carboxylic acid salt of sotalol.

14. The composition as defined by claim 9, wherein (i) is a systemically therapeutically effective unit β-adrenergic blocking amount of a long chain carboxylic acid salt of oxprenolol.

15. The composition as defined by claim 9, wherein (i) is a systemically therapeutically effective unit β-adrenergic blocking amount of a long chain carboxylic acid salt of pindolol.

16. The composition as defined by claim 9, wherein (i) is a systemically therapeutically effective unit β-adrenergic blocking amount of a long chain carboxylic acid salt of metoprolol.

17. The composition as defined by claim 9, wherein (i) is a systemically therapeutically effective unit β-adrenergic blocking amount of a long chain carboxylic acid salt of nadoxolol.

18. The composition as defined by claim 9, wherein (i) is a systemically therapeutically effective unit β-adrenergic blocking amount of a long chain carboxylic acid salt of practolol.

19. The composition as defined by claim 9, wherein (i) is a systemically therapeutically effective unit β-adrenergic blocking amount of a long chain carboxylic acid salt of butoxamine.

20. The composition as defined by claim 9, wherein (i) is a systemically therapeutically effective unit β-adrenergic blocking amount of a long chain carboxylic acid salt of alprenolol.

21. The composition as defined by claim 9, wherein (i) is a systemically therapeutically effective unit β-adrenergic blocking amount of a long chain carboxylic acid salt of metalol.

22. The composition as defined by claim 9, wherein (i) is a systemically therapeutically effective unit β-adrenergic blocking amount of a long chain carboxylic acid salt of nifenalol.

23. The composition as defined by claim 9, wherein (i) is a systemically therapeutically effective unit β- adrenergic blocking amount of a long chain carboxylic acid salt of acebutolol.

24. The composition as defined by claim 9, wherein (i) is a systemically therapeutically effective unit β-adrenergic blocking amount of a long chain carboxylic acid salt of atenolol.

25. The composition as defined by claim 9, wherein (i) is a systemically therapeutically effective unit β-adrenergic blocking amount of a long chain carboxylic acid salt of bunolol.

26. The composition as defined by claim 9, wherein (i) is a systemically therapeutically effective unit β-adrenergic blocking amount of a long chain carboxylic acid salt of carteolol.

27. The composition as defined by claim 9, wherein (i) is a systemically therapeutically effective unit β-adrenergic blocking amount of a long chain carboxylic acid salt of labetalol.

28. The composition as defined by claim 9, wherein (i) is a systemically therapeutically effective unit β-adrenergic blocking amount of a long chain carboxylic acid salt of pamatolol.

29. The composition as defined by claim 9, wherein (i) is a systemically therapeutically effective unit β-adrenergic blocking amount of a long chain carboxylic acid salt of timolol.

30. The composition as defined by claim 9, wherein (i) is a systemically therapeutically effective unit β-adrenergic blocking amount of a long chain carboxylic acid salt of tiprenolol.

31. The composition as defined by claim 9, wherein (i) is a systemically therapeutically effective unit β-adrenergic blocking amount of a long chain carboxylic acid salt of xipranolol.

32. The composition as defined by claim 9, wherein (i) is a systemically therapeutically effective unit β-adrenergic blocking amount of a long chain carboxylic acid salt of bupranolol.

33. The composition as defined by claim 9, said composition being in the form of a nasal ointment.

34. The composition as defined by claim 9, said composition being in the form of a nasal gel.

35. A pharmaceutically acceptable nasal composition, in dosage unit form, for nasal administration to obtain a systemic therapeutic β-adrenergic blocking response in a warm-blooded animal, consisting essentially of, per nasal dosage unit, (i) a systemically therapeutically effective unit β-adrenergic blocking amount of dichloroisoproterenol, pronethalol, sotalol, oxprenolol, pindolol, metoprolol, nadoxolol, practolol, butoxamine, alprenolol, metalol, nifenalol, acebutolol, atenolol, bunolol, carteolol, labetalol, pamatolol, timolol, tiprenolol, xipranolol or bupranolol, or a nontoxic pharmaceutically acceptable salt thereof, and (ii) a nontoxic pharmaceutically acceptable nasal carrier therefor, said composition being in the form of a nasal ointment or a nasal gel adapted for sustained release to the nasal mucosa.

36. The composition as defined by claim 35, said composition being in the form of a nasal ointment.

37. The composition as defined by claim 35, said composition being in the form of a nasal gel.

38. The composition as defined by claim 35, wherein (i) is a systemically therapeutically effective unit β-adrenergic blocking amount of dichloroisoproterenol or a nontoxic pharmaceutically acceptable acid addition salt thereof.

39. The composition as defined by claim 35, wherein (i) is a systemically therapeutically effective unit β-adrenergic blocking amount of pronethalol or a nontoxic pharmaceutically acceptable acid addition salt thereof.

40. The composition as defined by claim 35, wherein (i) is a systemically therapeutically effective unit β-adrenergic blocking amount of sotalol or a nontoxic pharmaceutically acceptable acid addition salt thereof.

41. The composition as defined by claim 35, wherein (i) is a systemically therapeutically effective unit β-adrenergic blocking amount of oxprenolol or a nontoxic pharmaceutically acceptable acid addition salt thereof.

42. The composition as defined by claim 35, wherein (i) is a systemically therapeutically effective unit β-adrenergic blocking amount of pindolol or a nontoxic pharmaceutically acceptable acid addition salt thereof.

43. The composition as defined by claim 35, wherein (i) is a systemically therapeutically effective unit β-adrenergic blocking amount of metoprolol or a nontoxic pharmaceutically acceptable acid addition salt thereof.

44. The composition as defined by claim 35, wherein (i) is a systemically therapeutically effective unit β-adrenergic blocking amount of nadoxolol or a nontoxic pharmaceutically acceptable acid addition salt thereof.

45. The composition as defined by claim 35, wherein (i) is a systemically therapeutically effective unit β-adrenergic blocking amount of practolol or a nontoxic pharmaceutically acceptable acid addition salt thereof.

46. The composition as defined by claim 35, wherein (i) is a systemically therapeutically effective unit β-adrenergic blocking amount of butoxamine or a nontoxic pharmaceutically acceptable acid addition salt thereof.

47. The composition as defined by claim 35, wherein (i) is a systemically therapeutically effective unit β-adrenergic blocking amount of alprenolol or a nontoxic pharmaceutically acceptable acid addition salt thereof.

48. The composition as defined by claim 35, wherein (i) is a systemically therapeutically effective unit β-adrenergic blocking amount of metalol or a nontoxic pharmaceutically acceptable acid addition salt thereof.

49. The composition as defined by claim 35, wherein (i) is a systemically therapeutically effective unit β-adrenergic blocking amount of nifenalol or nontoxic pharmaceutically acceptable acid addition salt thereof.

50. The composition as defined by claim 35, wherein (i) is a systemically therapeutically effective unit β-adrenergic blocking amount of acebutolol or a nontoxic pharmaceutically acceptable acid addition salt thereof.

51. The composition as defined by claim 35, wherein (i) is a systemically therapeutically effective unit β-adrenergic blocking amount of atenolol or a nontoxic pharmaceutically acceptable acid addition salt thereof.

52. The composition as defined by claim 35, wherein (i) is a systemically therapeutically effective unit β-adrenergic blocking amount of bunolol or a nontoxic pharmaceutically acceptable acid addition salt thereof.

53. The composition as defined by claim 35, wherein (i) is a systemically therapeutically effective unit β-adrenergic blocking amount of carteolol or a nontoxic pharmaceutically acceptable acid addition salt thereof.

54. The composition as defined by claim 35, wherein (i) is a systemically therapeutically effective unit β-adrenergic blocking amount of labetalol or a nontoxic pharmaceutically acceptable acid addition salt thereof.

55. The composition as defined by claim 35, wherein (i) is a systemically therapeutically effective unit β-adrenergic blocking amount of pamatolol or a nontoxic pharmaceutically acceptable acid addition salt thereof.

56. The composition as defined by claim 35, wherein (i) is a systemically therapeutically effective unit β-adrenergic blocking amount of timolol or a nontoxic pharmaceutically acceptable acid addition salt thereof.

57. The composition as defined by claim 35, wherein (i) is a systemically therapeutically effective unit β-adrenergic blocking amount of tiprenolol or a nontoxic pharmaceutically acceptable acid addition salt thereof.

58. The composition as defined by claim 35, wherein (i) is a systemically therapeutically effective unit β-adrenergic blocking amount of xipranolol or a nontoxic pharmaceutically acceptable acid addition salt thereof.

59. The composition as defined by claim 35, wherein (i) is a systemically therapeutically effective unit β-adrenergic blocking amount of bupranolol or a nontoxic pharmaceutically acceptable acid addition salt thereof.

60. A long chain carboxylic acid salt of dichloroisoproterenol, pronethalol, sotalol, oxprenolol, pindolol, metoprolol, nadoxolol, practolol, butoxamine, alprenolol, metalol, nifenalol, acebutolol, atenolol, bunolol, carteolol, labetalol, pamatolol, timolol, tiprenolol, xipranolol or bupranolol, the carboxylic acid portion of said salt containing 10 to 20 carbon atoms.

61. A salt as defined by claim 60, said salt being a stearate.

* * * * *